(12) United States Patent
Bridwell et al.

(10) Patent No.: US 7,794,464 B2
(45) Date of Patent: Sep. 14, 2010

(54) SPINAL DEROTATION INSTRUMENTS AND METHODS

(75) Inventors: Keith Bridwell, St. Louis, MO (US);
Stewart Young, Memphis, TN (US);
Brian Burd, Memphis, TN (US);
Douglas D. Kave, Byhalia, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 681 days.

(21) Appl. No.: 11/350,914

(22) Filed: Feb. 9, 2006

(65) Prior Publication Data
US 2007/0213715 A1    Sep. 13, 2007

(51) Int. Cl.
*A61F 5/00* (2006.01)
*A61B 17/70* (2006.01)

(52) U.S. Cl. .................. 606/86 A; 606/265; 606/279; 606/914

(58) Field of Classification Search .............. 606/246, 606/250, 252, 265, 277, 278, 54, 253–257, 606/260, 279, 99, 86 A, 914
See application file for complete search history.

(56) References Cited

U.S. PATENT DOCUMENTS

| | | | |
|---|---|---|---|
| 4,409,968 A | 10/1983 | Drummond |
| 4,505,268 A | 3/1985 | Sgandurra |
| 5,020,519 A | 6/1991 | Hayes et al. |
| 5,102,412 A | 4/1992 | Rogozinski |
| 5,176,679 A | 1/1993 | Lin |
| 5,181,917 A | 1/1993 | Rogozinski |
| 5,196,013 A | 3/1993 | Harms et al. |
| 5,219,349 A | 6/1993 | Krag et al. |
| 5,261,907 A | 11/1993 | Vignaud et al. |
| 5,281,223 A | 1/1994 | Ray |
| 5,385,565 A | 1/1995 | Ray |
| 5,425,732 A | 6/1995 | Ulrich |
| 5,437,669 A | 8/1995 | Yuan et al. |
| 5,478,340 A | 12/1995 | Kluger |
| 5,531,747 A | 7/1996 | Ray |
| 5,545,166 A | 8/1996 | Howland |
| 5,591,165 A | 1/1997 | Jackson |
| 5,632,744 A | 5/1997 | Campbell, Jr. |
| 5,649,926 A | 7/1997 | Howland |
| 5,672,175 A | 9/1997 | Martin |
| 5,702,392 A | 12/1997 | Wu et al. |
| 5,702,457 A | 12/1997 | Walch et al. |
| 5,704,937 A | 1/1998 | Martin |
| 5,707,371 A | 1/1998 | Metz-Stavenagen |

(Continued)

FOREIGN PATENT DOCUMENTS

DE        87 12 943 U1    11/1987

(Continued)

*Primary Examiner*—Eduardo C Robert
*Assistant Examiner*—Ellen Rust

(57) ABSTRACT

Derotation instrument assemblies and systems are provided to facilitate positioning one or more vertebrae of a spinal column into a desired alignment. The instrument assemblies and systems include implant holders engageable to respective implants engaged to vertebrae of the spinal column, transverse bridges to connect implant holders associated with a particular vertebra, and inter-level linking assemblies to connect instrument assemblies associated with different vertebrae. Derotation handles can be provided to facilitate application of the alignment forces, while the assemblies distribute the corrective forces to the connected implants and vertebrae.

32 Claims, 14 Drawing Sheets

U.S. PATENT DOCUMENTS

| | | | |
|---|---|---|---|
| 5,733,284 | A | 3/1998 | Martin |
| 5,797,910 | A | 8/1998 | Martin |
| 5,814,046 | A | 9/1998 | Hopf |
| 6,015,409 | A | 1/2000 | Jackson |
| 6,090,113 | A | 7/2000 | LeCouedic et al. |
| 6,171,311 | B1 | 1/2001 | Richelsoph |
| 6,251,112 | B1 | 6/2001 | Jackson |
| 6,402,753 | B1 | 6/2002 | Cole et al. |
| 6,458,131 | B1 | 10/2002 | Ray |
| 6,511,484 | B2 | 1/2003 | Torode et al. |
| 6,565,568 | B1 | 5/2003 | Rogozinski |
| 6,605,088 | B1 | 8/2003 | St. Onge et al. |
| 6,648,888 | B1 | 11/2003 | Shluzas |
| 6,726,692 | B2 | 4/2004 | Bette |
| 6,749,613 | B1 | 6/2004 | Conchy et al. |
| 6,755,828 | B2 | 6/2004 | Shevtsov et al. |
| 6,916,319 | B2 * | 7/2005 | Munting .................. 606/278 |
| 6,945,933 | B2 | 9/2005 | Branch et al. |
| 7,004,947 | B2 | 2/2006 | Shluzas et al. |
| 7,090,679 | B2 * | 8/2006 | Saint-Martin et al. ......... 606/99 |
| 7,371,239 | B2 | 5/2008 | Dec et al. |
| 7,465,306 | B2 | 12/2008 | Pond, Jr. et al. |
| 2003/0144665 | A1 | 7/2003 | Munting |
| 2003/0225408 | A1 | 12/2003 | Nichols et al. |
| 2004/0034350 | A1 | 2/2004 | St. Onge et al. |
| 2004/0172022 | A1 | 9/2004 | Landry et al. |
| 2004/0249378 | A1 | 12/2004 | Saint Martin et al. |
| 2005/0033291 | A1 | 2/2005 | Ebara |
| 2005/0033299 | A1 | 2/2005 | Shluzas |
| 2005/0149036 | A1 | 7/2005 | Varieur et al. |
| 2005/0149053 | A1 | 7/2005 | Varieur et al. |
| 2005/0159757 | A1 | 7/2005 | Shluzas et al. |
| 2005/0171540 | A1 | 8/2005 | Lim et al. |
| 2005/0182400 | A1 | 8/2005 | White |
| 2005/0245928 | A1 | 11/2005 | Colleran et al. |
| 2006/0106380 | A1 * | 5/2006 | Colleran et al. ............... 606/61 |
| 2006/0149236 | A1 | 7/2006 | Barry |
| 2006/0195092 | A1 | 8/2006 | Barry |
| 2006/0271050 | A1 | 11/2006 | Piza |
| 2007/0093846 | A1 | 4/2007 | Frigg et al. |
| 2007/0161989 | A1 * | 7/2007 | Heinz et al. ................... 606/61 |
| 2007/0173827 | A1 | 7/2007 | Morrison et al. |
| 2007/0213715 | A1 | 9/2007 | Bridwell et al. |
| 2007/0213716 | A1 | 9/2007 | Lenke et al. |

FOREIGN PATENT DOCUMENTS

| | | |
|---|---|---|
| EP | 0528177 A2 * | 7/1992 |
| EP | 0 528 177 A2 | 2/1993 |
| EP | 0602351 A1 * | 10/1993 |
| EP | 0 602 351 A1 | 6/1994 |
| EP | 1 269 930 A2 | 1/2003 |
| WO | WO 90/02527 | 3/1990 |
| WO | WO 91/06254 | 5/1991 |
| WO | WO 02/094114 A1 | 11/2002 |
| WO | WO 02094114 A1 * | 11/2002 |
| WO | WO 2005/058141 A2 | 6/2005 |

* cited by examiner

SPINAL DEROTATION INSTRUMENTS AND METHODS

BACKGROUND

Surgical correction of the positioning and alignment of one or more vertebrae in the spinal column can be desired to address various pathologies and conditions of patients. However, such repositioning and re-alignment can be time-consuming, cumbersome, and potentially difficult to achieve during a surgical procedure. For example, the alignment of multiple vertebral levels can require manipulation of instrumentation at each level to achieve the desired results. Forces applied to the vertebral body need to be controlled to minimize stresses on the vertebral bodies and implants. Furthermore, the alignment at one level should be maintained while other levels are aligned. In addition, the instrumentation employed to achieve the alignment can hinder placement of stabilization constructs that post-operatively maintain the corrected positioning and alignment achieved during surgery.

Therefore, instruments, methods and systems that facilitate surgical correction of the alignment and positioning of a vertebra or vertebrae of the spinal column would be desirable. Furthermore, instruments, methods and systems that facilitate placement of stabilization constructs that post-operatively maintain the corrected vertebra or vertebrae are also desirable. In addition, instruments, methods and systems that facilitate control of the stress exerted on implants and vertebrae to which the implants are attached would be desirable.

DETAILED DESCRIPTION OF THE ILLUSTRATED EMBODIMENTS

Figure 1:
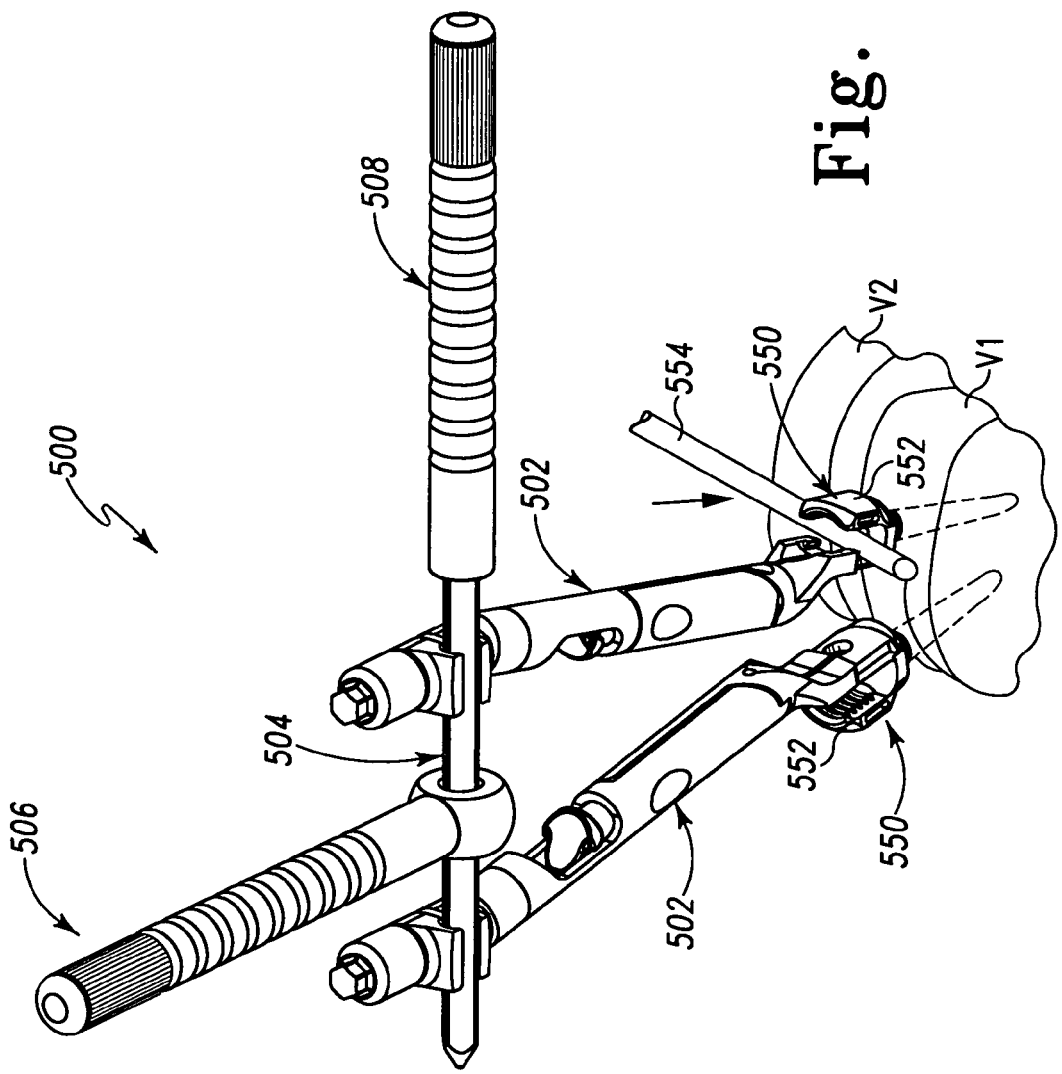
FIG. 1 is a perspective view of a derotation instrument assembly coupled to implants engaged to a vertebra.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Spinal derotation instrumentation is provided to affect one or more derotation maneuvers on a scoliotic spine or on a spine having one or more displaced, misaligned or curved vertebral levels. Specifically, a derotation instrument assembly is attached to at least one vertebral body, with the assembly including at least one bone implant anchored to the vertebral body along at least on of the left and right sides of the spinal column; an elongate implant holder removably attached to a head portion of the at least one bone implants. In embodiments employing multiple implants engaged to a vertebral body, a transverse bridge interconnects the proximal end portions of the implant holders and a primary handle extending axially from a central portion of the transverse bridge in a direction generally parallel with the sagittal plane and implant holders for manipulation by the surgeon. One or more in-line de-rotation handles can be engaged to respective ones of the implant holders to allow selective manipulation of an implant holder and implant.

The derotation instrument assembly may also include a secondary handle, either along or in combination with the primary handle, extending laterally from an end portion of the transverse bridge (e.g., in a direction generally perpendicular or substantially transverse to the implant holders and sagittal plane) for further manipulation by the surgeon. The secondary handle may be threadingly or otherwise suitably removably engaged to the transverse bridge to allow for selective attachment and removal. In an alternative embodiment of the derotation instrumentation, the transverse bridge may be eliminated, and a manipulation handle may be engaged directly to the proximal end of each implant holder, such as by threading engagement to allow for selective attachment and removal, for individual manipulation of the implant holders by the surgeon.

The bone implants can be configured as pedicle screws, with each screw having a head portion which includes a pair of arms defining a U-shaped channel for receiving a spinal rod, and with the arms defining internal threads for threadingly receiving a set screw for capturing the spinal rod within the U-shaped channel. The screw can be uni-axial, or multi-axial so that the head can pivot relative to the bone engaging portion. In the illustrated embodiment, the head portions of the screws are configured to receive stabilization element either through a top opening between the pair of arms or to receive an end of the stabilization element as it is passed through the head in an end-wise manner. In another embodiment, the head portion of the screws opens to a side so that the stabilization element can be side-loaded therein. Other embodiments contemplate any suitable type of implant that can be engaged to a vertebra and coupled to an elongated stabilization element.

The elongate implant holders can each include a distal end portion configured for selective clamping to either arm of the screw head portion. In one specific embodiment, the implant holder includes a tubular body extending the length of the implant holder and a clamp portion pivotally attached at the distal end portion of the tubular body via a pivot pin. A spring may be included for biasing the clamp portion toward an open position along with a releasable latching mechanism to releasably capture the arm of the screw head portion between the distal end portions of the tubular body and the clamp portion. The implant holder may also include a release button to selectively release the tubular body and the clamp portion from the arm of the screw head portion. The implant holder can include a length so that at least its proximal end is positioned outside the patient through the wound or incision in which the vertebrae are accessed.

The proximal end of the implant holder can include a threaded post that is rotatably and pivotally coupled to the tubular body via a ball and socket joint to allow for angular adjustment therebetween. The threaded post of each implant holder is engaged to the transverse bridge via a clamping mechanism that is configured to slide along the length of an elongated connecting member at the transverse bridge. Such engagement between the implant holders and the transverse bridge allows for variable lateral adjustment and variable angular adjustment of the implant holders relative to the transverse bridge. The clamping assemblies can be provisionally tightened to the threaded post, and then finally tightened for secure engagement with a handle that serves as one of the derotation handles.

In one embodiment, the transverse bridge is configured as a plate defining an elongate slot extending therethrough, with the threaded post of each implant holder positioned within the elongate slot and extending through an aperture in a plate clamping assembly, which is in turn clamped onto opposite side portions of the plate via a knurled nut that is tightened onto the threaded post. The primary handle may be removably engaged to a central portion of the plate via a similarly-configured handle mount.

In another embodiment, the transverse bridge is configured as a diamond-shaped rod, with the threaded posts of each implant holder extending through an aperture in a rod clamping assembly, which is in turn clamped onto the diamond-shaped rod via a knurled nut tightened onto the threaded post. The primary handle may be removably engaged to a central portion of the diamond-shaped rod between the implant holders via a handle mount collar having a diamond-shaped aperture that can be fixed about or slidably receives the diamond-shaped rod. The primary handle can be engaged to the handle mount collar.

Still other embodiments contemplate a transverse bridge having other configurations. Such configurations include, but are not limited to, rack-and-pinion adjustment mechanisms, telescoping adjustment mechanisms, and turn buckle adjustment mechanisms. In still another embodiment, the transverse bridge can connect implant holders engaged to respective ones of two or more vertebrae, and extend across the spinal midline to link the implant holders to one another.

In instances requiring derotation across multiple vertebral levels, a derotation instrument assembly may be attached to respective ones of the multiple vertebral bodies requiring derotation, with the derotation instrument assemblies being interconnected by an inter-level linking assembly coupled between the individual derotation instrument assemblies. As a result, the surgeon may manipulate an integrated frame assembly to affect derotation across multiple vertebral levels, rather than separately manipulating several derotation instrument assemblies to effect derotation at each individual vertebral level. The transverse bridge assembly can be releasably coupled to the implants holders such that the spacing and angular orientation between implant holders can be readily adjusted and maintained with clamping assemblies that secure the implant holders to a bridge member extending between the implant holders. The inter-level linking assemblies can be releasably coupled to the primary handles, for example, such that the spacing and angular orientation between the primary handles and the linked derotation instrument assemblies can be readily adjusted and maintained with connector assemblies that secure the derotation instrument assemblies to an elongate link member extending between the derotation instrument assemblies.

In one embodiment, the inter-level linking member is coupled between the primary manipulation handles of the derotation instrument assemblies. However, the inter-level linking member may extend between other structures such as the clam ping assemblies that that connect the elongate implant holders to the transverse bridge or directly to the secondary handles. In a specific embodiment, the inter-level linking member includes an elongate rod that is coupled to the primary manipulation handles by a connector assembly that resembles a modified TSRH® 3D connector including a knurled nut for securing the connector to the primary manipulation handle.

The inter-level linking assemblies can interconnect the derotation instrument assemblies in a rigid fashion so that the engagement relationship between the components is maintained during derotation of the spinal column. It is further contemplated that at least limited slippage or movement between the inter-level linking assemblies and the derotation instrument assemblies can be provided as the spinal column is straightened to accommodate non-uniform relative displacement among the corrected vertebrae that may be required.

In FIG. 1 there is shown one embodiment of a derotation instrument assembly 500 coupled to implants 550. Implants 550 are engaged to a vertebral body V1. In one specific application, implants 550 are bone anchors secured to respective ones of the pedicles of vertebral body V1. Implants 550 each include a receiver portion 552 for receiving a respective elongated spinal stabilization element 554 positionable along the spinal column and securable to the implants to maintain a positioning of one or more vertebral bodies. In the illustrated embodiment, the implants are bone screws with a U-shaped head portion providing a receiver to receive a spinal rod. Other embodiments contemplate saddles, posts, clamping members, side-loading members or other receiver type members extending from a bone engaging portion in the form of a staple, hook, screw, interbody device, intrabody device or other bone engaging member.

Derotation instrument assembly 500 includes implant holders 502 removably engaged to respective ones of the implants 550 and extending proximally therefrom. The implant holders 502 can be interconnected with one another in a bilateral fashion with a transverse bridge 504 extending therebetween. Transverse bridge 504 includes a primary derotation handle 506 extending therefrom at a location between implant holders 502. Primary derotation handle 506 extends in a direction that is generally parallel to implant holders 502 and in a direction that is generally parallel to the sagittal plane of the spinal column. A secondary derotation handle 508 can extend from transverse bridge 504 in the same direction in which bridge 504 extends. Thus, secondary derotation handle 508 can extend in a transverse orientation to implant holders 502 and in a direction that is generally parallel to the coronal plane of the spinal column.

Derotation instrument assembly 500 can be manipulated with one or both of primary handle 506 and secondary handle 508 to displace, pull, twist or align the vertebra to which implants 550 is engaged into the desired alignment with the spinal column. Accordingly, manipulation of multiple anchors engaged to the spinal column can be completed with a single-handled approach, although the application of such forces through multiple handles is not precluded. For example, positioning of primary handle 506 in a medialized or central relation relative to the implants 550 results in the corrective forces being distributed to both implants and thus to multiple locations on the vertebral body. This can reduce stress concentrations at any single bone/implant interface as the manipulation forces are applied.

Figure 2:
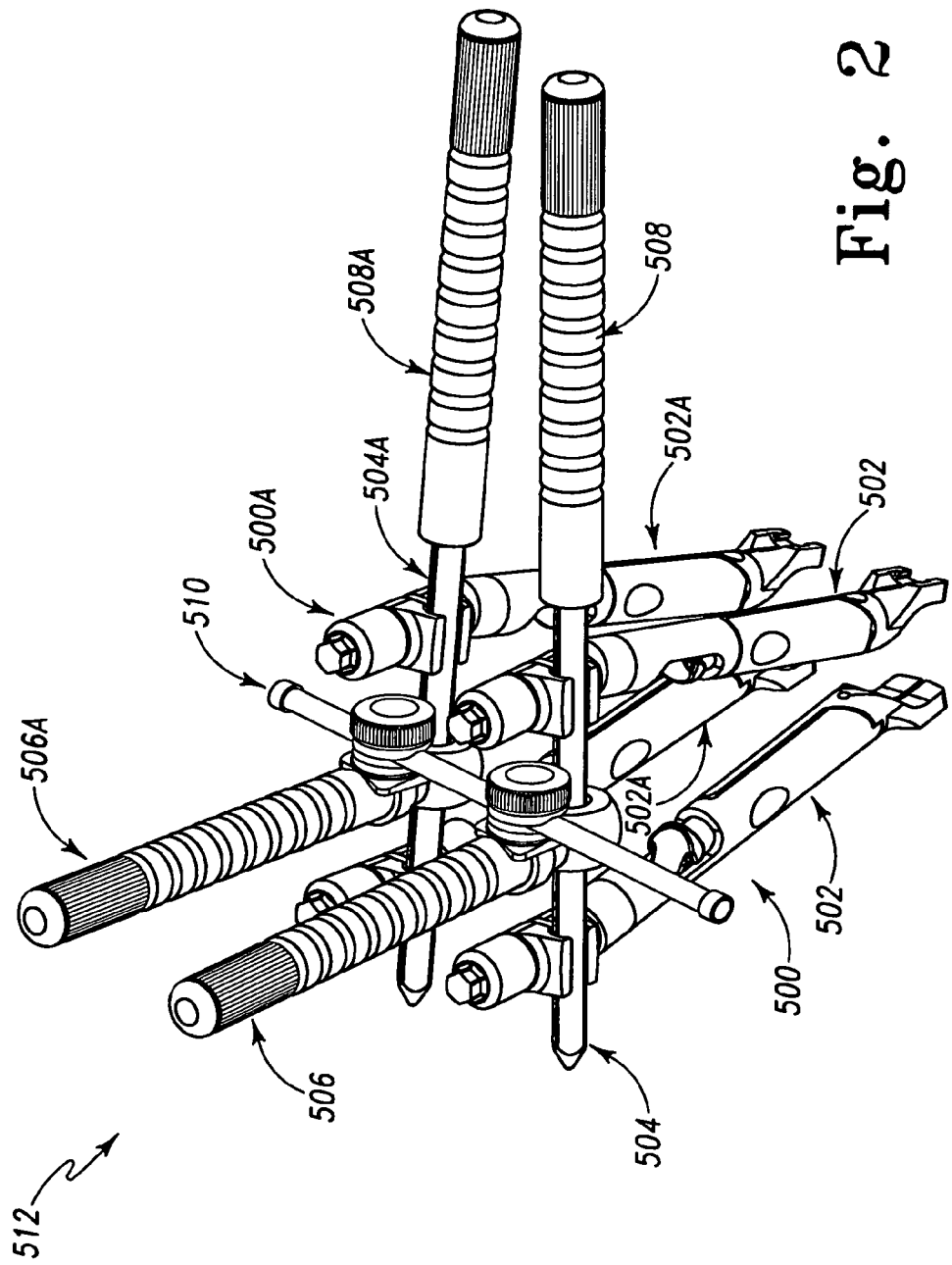
FIG. 2 is a perspective view of a derotation system for multiple vertebral levels.
Figure 3:
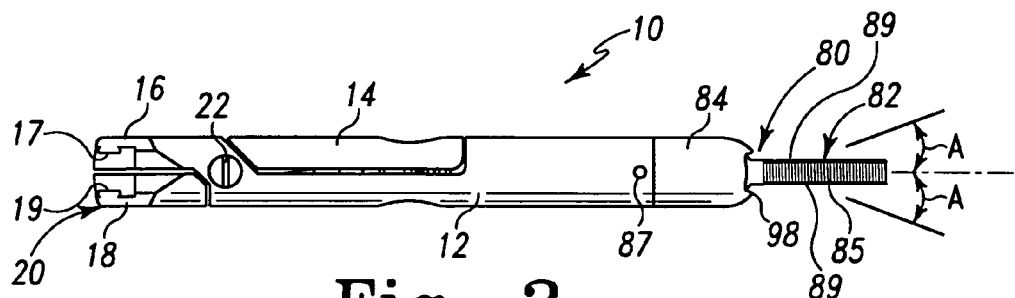
FIG. 3 is an elevation view of an implant holder of the derotation instrument assembly of FIG. 1 in a closed position.

It is further contemplated that a number of derotation instrument assemblies 500 can be coupled to one another by one or more inter-level linking assemblies 510 extending between and coupled to, for example, primary handles 506 and 506A of the respective assemblies 500 and 500A shown in FIG. 2. The inter-level, linked instrument assemblies 500, 500A provide a derotation system 512 that facilitates the application of and distribution of derotation, correction, alignment and other forces to various bony structures engaged by the bone implants and interconnected within the system. Accordingly, the resultant stress on any one of the implants and the bone to which the implant is engaged is distributed to multiple locations and/or multiple vertebrae. It is contemplated that any one, two or three or more vertebral levels with derotation instrument assemblies 500 can be linked. It is further contemplated that any subset of instrumented vertebral levels in a system could be linked. In addition or in lieu of linking primary handles 506, secondary handles 508, transverse bridge 504, and/or implant holders 502 could be linked.

Figure 4:
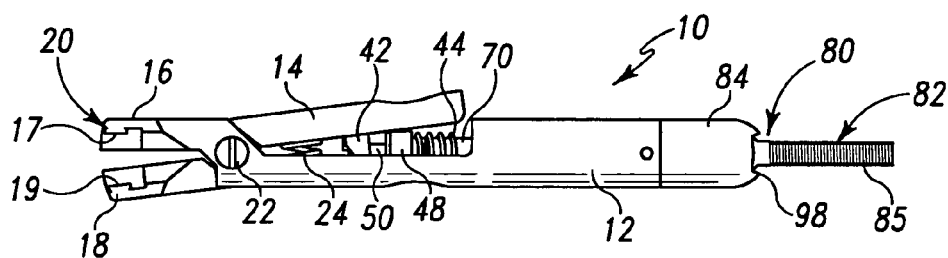
FIG. 4 is an elevation view of the implant holder of FIG. 3 in an open position.

Referring now to FIGS. 3-11, one specific example of implant holder 502 will be discussed with respect to an implant holder 10. Implant holder 10 includes a first arm 12 in the form of a tubular body and a second arm 14 providing a clamp portion pivotally coupled to first arm 12. Each of the first and second arms 12, 14 includes a respective distal end portion 16, 18 of a distal holding end 20 of implant holder 10. Each of the portions 16, 18 forms a space in which to receive a portion of the bone implant, and further includes a projection 17, 19 extending into the space toward the other portion 16, 18. The projections 17, 19 are received in detents formed in the receiver of the implant to which holder 10 is engaged by clamping arms 12, 14 to the receiver of the implant when implant holder 10 is closed, as shown FIG. 3 for example. To release the implant, implant holder 10 is opened by pivoting second arm 14 about pivotal connection 22 with first arm 12, as shown in FIG. 4.

Figure 5:
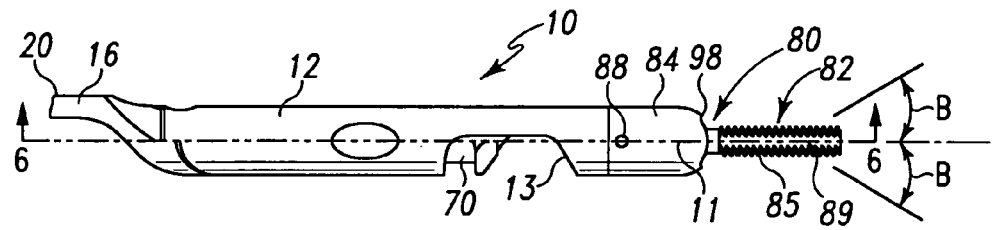
FIG. 5 is an elevation view of the implant holder of FIG. 3 rotated 90 degrees about its longitudinal axis.

Arms 12, 14 cross-over one another in a scissors type arrangement, and include inter-fitting recessed portions 30, 32, respectively, at connection 22 so that end portions 16, 18 are aligned with one another. Furthermore, as shown in FIG. 5, arms 12, 14 include a slight bend so that end portions 16, 18 are offset to one side of the longitudinal axis 11 of implant holder 10. In addition, the space between end portions 16, 18 opens away from axis 11 to so that the implant to which implant holder 10 is engaged can remain substantially unobstructed for engagement with another implant or system component.

Arms 12, 14 are spring biased toward the open position with a spring 24 positioned in wells 26, 28 formed by respective ones of the arms 12, 14. Wells 26, 28 are oriented toward one another, and located proximally of the pivotal connection 22 between arms 12, 14. In order to secure arms 12, 14 in the closed position in engagement with the implant, a latching mechanism 40 is provided between arms 12, 14. Latching mechanism 40 includes a latch member 42 extending from second arm 14 and a holding member 50 mounted to first arm 12 that is releasably engageable by latch member 42. Latching mechanism 40 also includes a release button 70 coupled to and extending proximally from holding member 50 between arms 12, 14, and a spring 44 biasing holding member 50 into engagement with latch member 42 and further biasing release button 70 proximally.

First arm 12 includes a collar 48 extending therefrom into a receptacle defined between arms 12, 14 in which latching mechanism 40 is located Holding member 50 extends through collar 48 and is axially movable therein while collar 48 maintains holding member 50 in axial alignment with the remaining portions of latching mechanism 40. In addition, an alignment pin 46 can be press fit in collar 48 and extend therefrom into a slot 52 (FIG. 10) along a portion of the length of holding member 50 to maintain holding member 50 in rotational alignment with latching mechanism 40. Other embodiments contemplate that collar 48 and/or alignment pin 46 can be eliminated.

Figure 6:
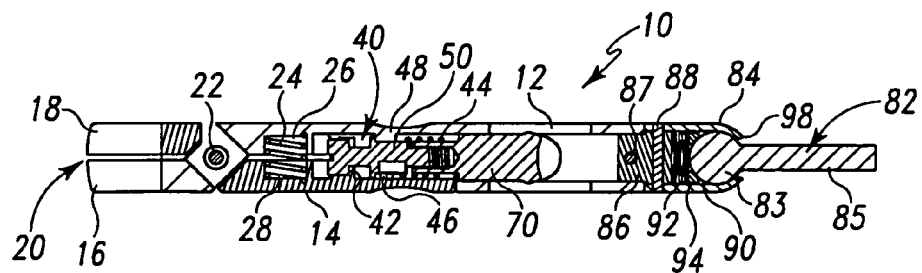
FIG. 6 is a section view along line 6-6 of FIG. 5.
Figure 9:
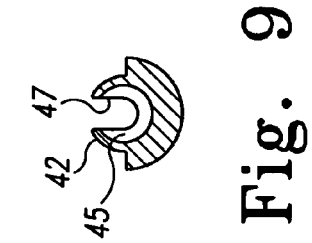
FIG. 9 is a sectional view looking proximally at a latch member of the implant holder of FIG. 3.
Figure 10:
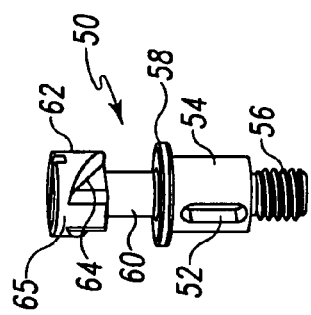
FIG. 10 is a perspective view of a holding member of the implant holder of FIG. 3.
Figure 7:
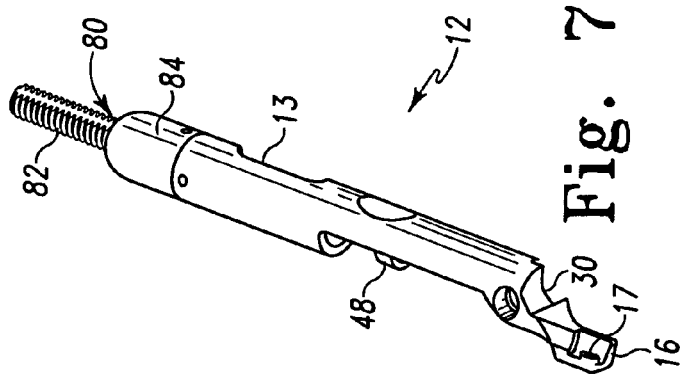
FIG. 7 is a perspective view of a first arm of the implant holder of FIG. 3.
Figure 12:
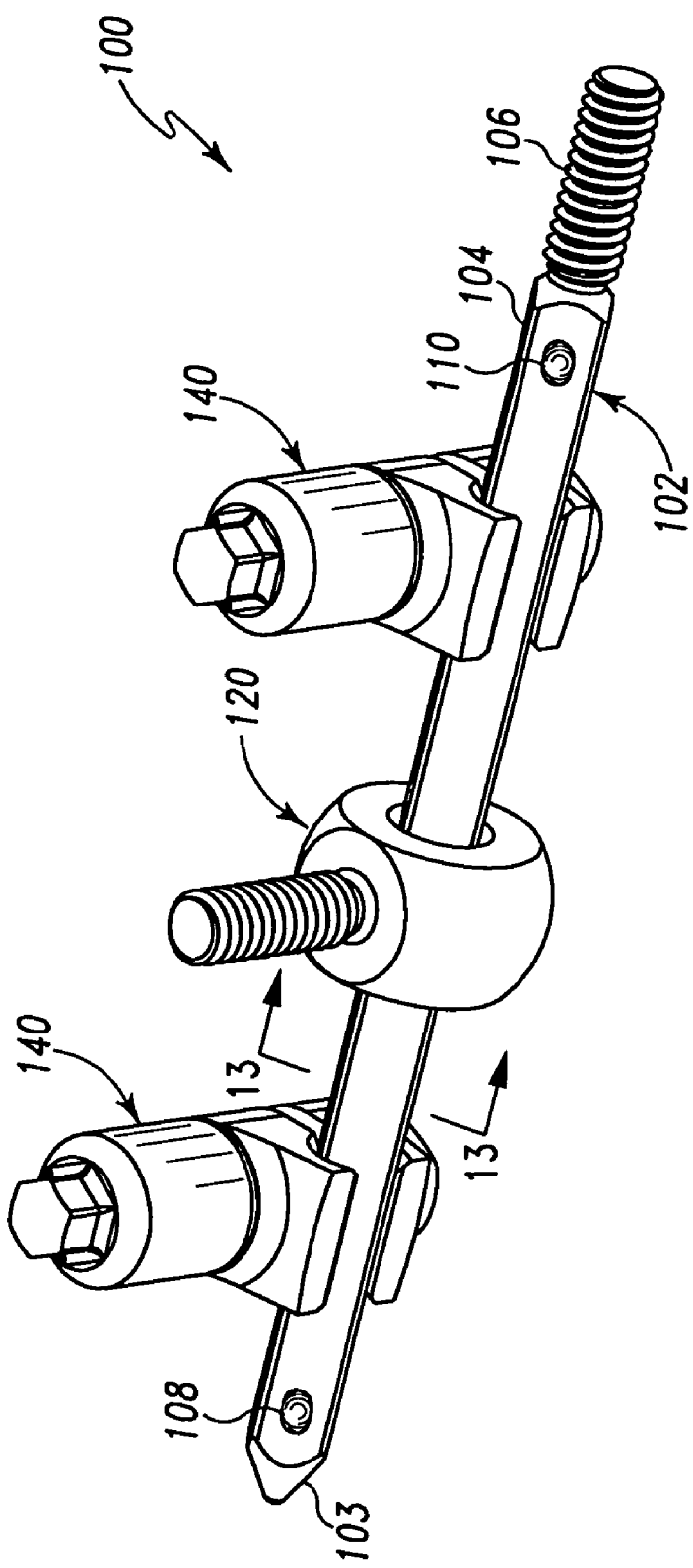
FIG. 12 is a perspective view of a transverse bridge with clamping assemblies of the derotation instrument assembly of FIG. 1.

Holding member 50 is shown in further detail in FIG. 10. Holding member 50 includes a central body 54 defining axial slot 52 therealong. A connector portion 56 extends from a proximal end of central body 54, and is threadingly received in a distal end opening of release button 70, as shown in FIG. 6. The distal end of central body 54 includes a radially outwardly extending flange 58 that abuttingly engages collar 48 to limit the proximal displacement of release button 70 and holding member 50 under the bias of spring 44.

Figure 8:
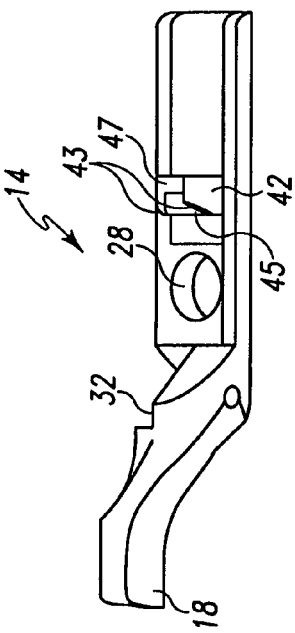
FIG. 8 is a perspective view of a second arm of the implant holder of FIG. 3.

Holding member 50 also includes a stem 60 extending distally from flange 58 to a latch receiving member 62. Latch receiving member 62 includes a cylindrical body with inclined notched areas 64 and a central projecting area 65 between inclined notched areas 64. In the open position, latch member 42 includes sloped portions 43 that reside along inclined notched areas 64, as shown in FIG. 8. When closing arms 12, 14 to engage the implant between portions 16, 18, the sloped portions 43 slide along the respective adjacent inclined notched areas 64 to distally and axially displace holding member 50 until the receptacle 45 (FIG. 9) of latch member 42 aligns with and receives the cylindrical body of latch receiving member 62, as shown in FIG. 6. In the closed position, arm 14 is prevented from pivoting away from arm 12 by engagement of latch member 42 around receiving member 62 of holding member 50. To release latch mechanism 40 and allow arm 14 to pivot away from arm 12, release button 70 is depressed to displace holding member 50 distally sufficiently to align stem 60 with slotted opening 47 (FIG. 9) of latch member 42. This allows receptacle 45 to become disengaged or displaced from about latch receiving member 62, and spring 44 pushes arm 14 away from arm 12 and rotates arm 14 about connection 22 to the open position of FIG. 4.

Figure 11:
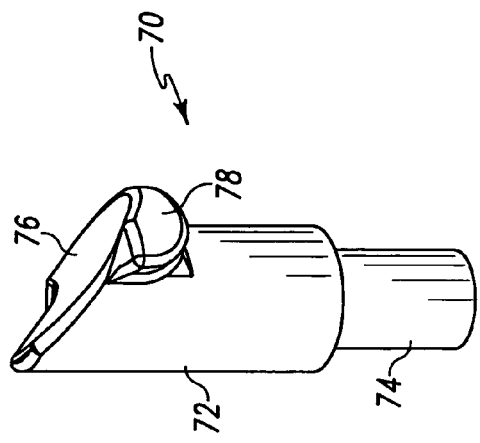
FIG. 11 is a perspective view of a release button of the implant holder of FIG. 3.

Release button 70 is further shown in FIG. 11, and includes a body portion 72 extending between a distal end member 74 and a proximal end 76. Distal end member 74 defines the opening which receives connector portion 56 of holding member 50. Proximal end 76 includes a concavely curved surface to facilitate application of manual depression forces with a thumb or finger to proximally displace button 70 and thus latch mechanism 40 between arms 12, 14. Button 70 is accessible through a notched area 13 of first arm 12, as shown in FIG. 5. An outwardly extending lip 78 adjacent proximal end 76 can contact first arm 12 in notched area 13 to maintain alignment of release button 70 as it is moved therein and to limit distal displacement of button 70.

Implant holder 10 further includes a proximal coupling mechanism 80. Coupling mechanism 80 includes a post 82 pivotal relative to first arm 12, and captured thereon with an end cap 84. Coupling mechanism 80 includes a base member 86 engaged to first arm 12 with a first pin 87. End cap 84 is coupled to base member 86 with a second pin 88. End cap 84 defines a receptacle 90 in which a spring 92 is positioned. A washer 94 is positioned against spring 92 opposite base member 86. Post 82 includes a ball end 83 that rests against washer 94, and post portion 85 extends through a proximal end opening 98 of end cap 84.

End opening 98 can be of any suitable shape and size to permit post portion 85 to extend therethrough. End opening 98 of end cap 84 can include a non-circular shape. For example, end opening 96 can be oval in shape such that in one direction relative to longitudinal axis 11, post 82 can be pivoted up to an angle A, and in the transverse direction post 82 can be pivoted up to angle B relative to longitudinal axis 11. In one specific embodiment, angle A can range from 0 degrees to 15 degrees, and angle B can range from 0 degrees to 30 degrees. The convexly curved shape at the proximal end of end cap 84 can receive components of the system, such as a clamping assembly 140, in any one of a number of angular orientations relative to longitudinal axis 11. In addition, ball end 83 can rotate on washer 94 during such pivoting. Spring 92 biases ball end 83 of post 82 proximally against the inner wall surface of end cap 84. The inner wall surface can include a concavely curved shape that extends around a portion of ball end 83 to facilitate rotation of ball end 83 thereagainst and thus the pivoting movement of post 82.

Post 82 can include opposite flat surfaces 89 extending therealong. Flat surface can be provided so that components of the system being secured to post 82 are non-rotatable relative thereto during such engagement. For example, clamp assembly 140 can include a keyed bore portion 143 (FIG. 16) that receives post 82 and flat surface 89 in form fitting engagement.

Referring now to FIGS. 12-16, one specific example of a transverse bridge 504 is shown in the form of transverse bridge 100. Transverse bridge 100 includes a transverse connecting member 102, a handle mount 120 positioned about transverse connecting member 102, and a pair of clamping assemblies 140 positioned about transverse connecting member 102 on opposite sides of handle mount 120. Handle mount 120 can either be fixed or slidable along connecting member 102, and clamping assemblies 140 can be slidably repositioned along transverse connecting member 102. Clamping assemblies 140 can be clamped against transverse connecting member 102 to maintain there respective positioning therealong.

Figure 13:
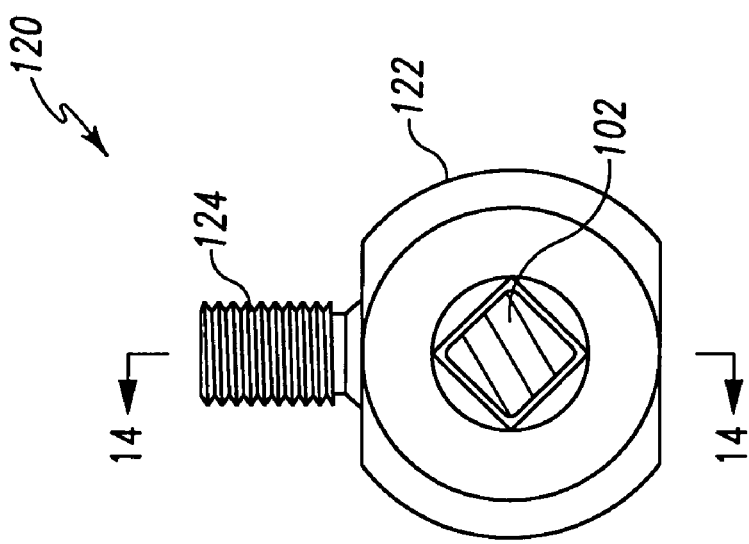
FIG. 13 is a section view through line 13-13 of FIG. 12 and showing a handle mount positioned about the link member of the transverse bridge.

Transverse connecting member 102 can have a diamond shaped cross-section as shown in section view in FIG. 13. Other cross-sectional shapes are also contemplated, including circular, square, rectangular, polygonal, and non-circular shapes, for example. Connecting member 102 extends between a first end 103 and a second end 104. First end 103 can be tapered as shown to facilitate placement of handle mount 120 and clamping assemblies 140 thereover. A non-tapered first end 103 is also contemplated. Second end 104 can include a connector portion 106 for connection with a transverse secondary handle. In the illustrated embodiment, connector portion 106 is a threaded end member. Other configurations for a connector portion 106 are also contemplated. Still other embodiments contemplate that a connector portion 106 is not provided. For example, a secondary handle can be provided that is integrally formed with connecting member 102. In another embodiment, a transverse secondary handle can be clamped or otherwise secured directly to the rod portion of connecting member 102 without a connector portion 106 on connecting member 102. Still further, a transverse secondary handle connected to connecting member 102 can be omitted for one or more of the transverse bridges of a derotation system.

Transverse connecting member 102 can further include first retaining member 108 and second retaining member 110. Retaining members 108, 110 can resist or prevent the handle mount 120, if slidable, and clamp assemblies 140 from sliding off the end of connecting member 102 during use and manipulation of the surgical system. In one embodiment, retaining members 108, 110 are spring-biased ball-plunger type mechanisms that can be forced into respective holes in connecting member 102 upon application of sufficient force to overcome the spring bias of the projecting ball member. However, the spring force is sufficient to maintain the ball member projecting from the recess when contacted by a clamping assembly 140 or handle mount 120 sliding along connecting member 102.

Figure 14:
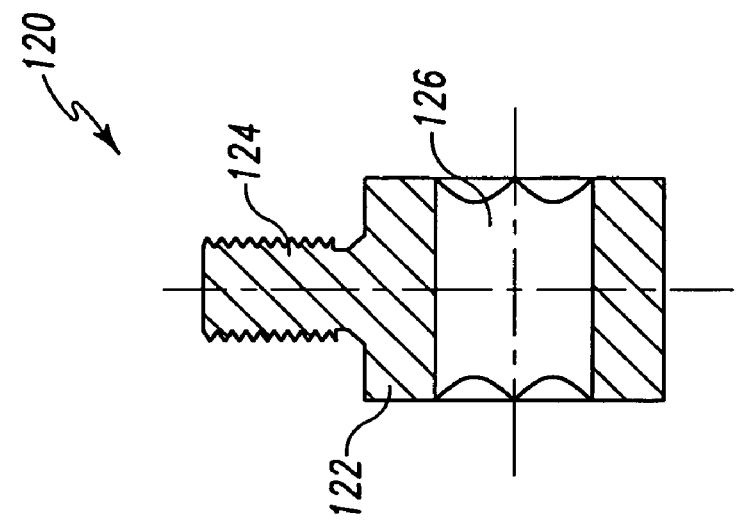
FIG. 14 is a section view through line 14-14 of FIG. 13 with the link member removed from the handle mount.

Handle mount 120 is shown in FIGS. 13-14, and includes a body portion 122 and a connector portion 124 extending from body portion 122. Body portion 122 defines a passage 126 through which transverse connecting member 102 extends. It is noted that connecting member 102 is removed in FIG. 14 for clarity in showing passage 126. Passage 126 can include a cross-sectional shape that mimics the shape of connecting member 102 to resist handle mount 120 from rotating about connecting member 102, and to facilitate the application of correction forces with a handle secured to handle mount 120. Handle mount 120 can be slidably positionable or fixed in position along connecting member 102.

Figure 16:
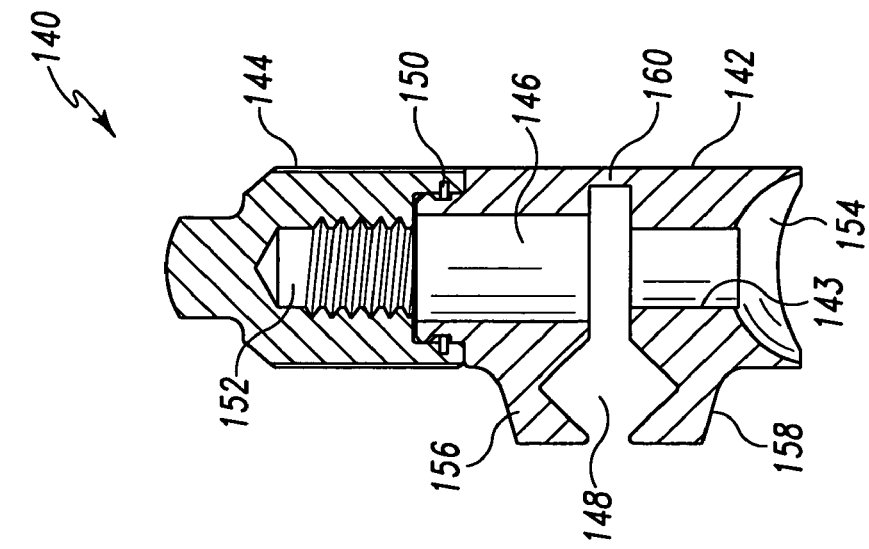
FIG. 16 is a section view of the clamping assembly through line 16-16 of FIG. 15.
Figure 15:
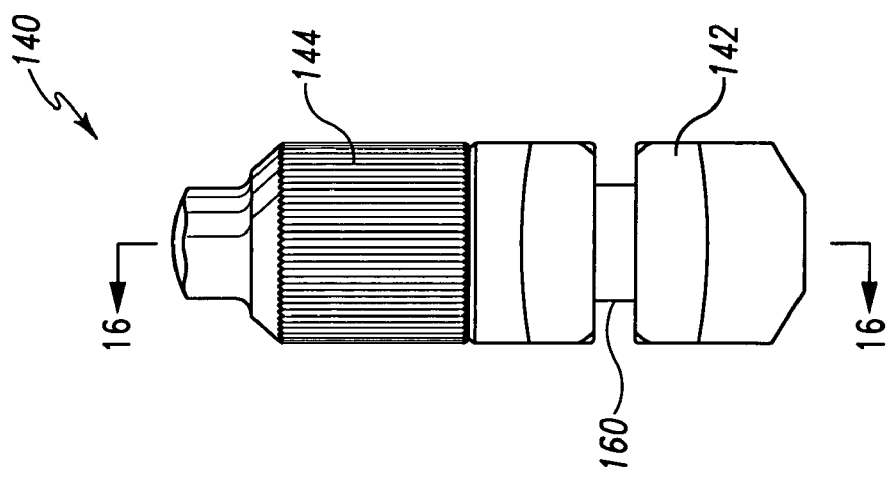
FIG. 15 is an elevation view of a clamping assembly of FIG. 12.

Referring now to FIGS. 15-16, clamping assembly 140 is shown in further detail. Clamping assembly 140 includes a clamping portion 142 and a securing portion 144 that is operable to secure and release clamping portion 142 to transverse connecting member 102. Clamping portion 142 includes a bore 146 for receiving proximal post 82 of the respective adjacent implant holder 10 discussed above. Bore 146 includes keyed portion 143 to non-rotatably receive post 82 in form fitting engagement. Clamping portion 142 further includes a passage 148 alignable with passage 126 of handle mount 120 to receive connecting member 102 in a transverse orientation to implant holder 10. Passage 148 is defined by and between clamping arms 156, 158, which are movable toward one another to secure connecting member 102 therebetween. Specifically, clamping portion 142 includes a living or integral hinge 160 opposite arms 156, 158 to facilitate such movement.

Securing portion 144 is rotatably retained and captured on a proximal end of clamping portion 142 with a retaining ring 150. Securing portion 144 includes a threaded bore 152 that can threadingly engage the proximal post 82 of implant holder 10. In use, the distal end 154 of clamping portion 142 is positioned in abutting engagement with the end cap 84 at the proximal end of implant holder 10 with post 82 extending through bore 146 for engagement in bore 152 of securing portion 144. As securing portion 144 is rotated and threaded distally along post 82 of implant holder 10, arms 156, 158 move about hinge 160 since clamping portion 142 is pressed between the proximal end cap 84 of implant holder 10 and securing portion 144. Securing portion 144 can be threaded proximally along post 82 to loosen or unclamp clamping portion 142 from connecting member 102 and allow repositioning of clamping assembly 140 along connecting member 102.

Figure 17A:
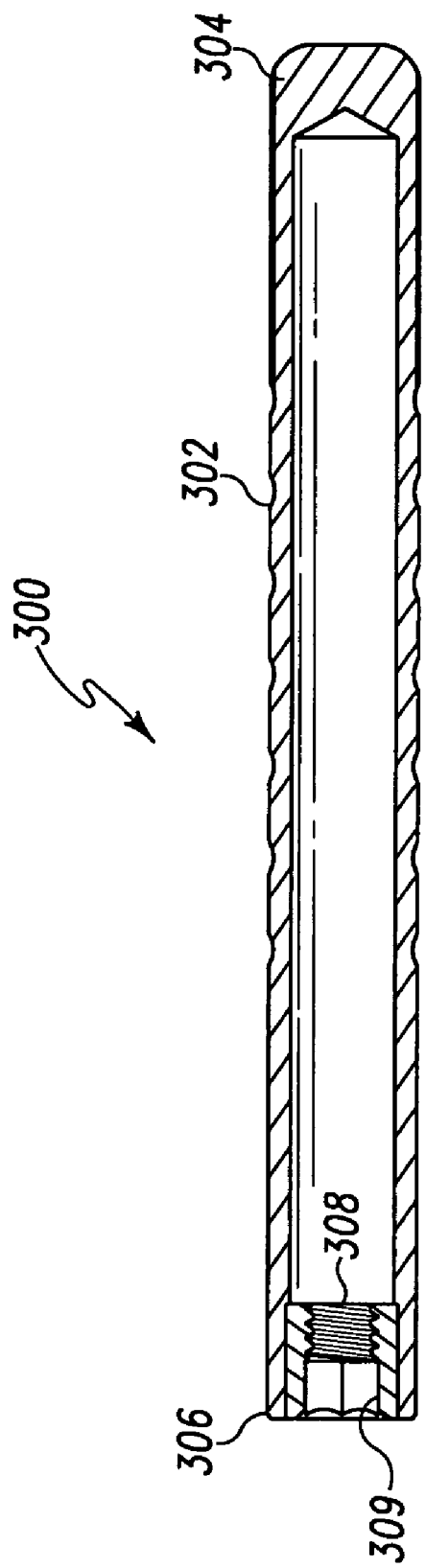
FIG. 17A is a longitudinal section view of a derotation handle.

Referring now to FIG. 17A, a longitudinal section view of one embodiment for the primary and secondary derotation handles 506, 508 is shown in the form of derotation handle 300. Primary handle 300 includes an elongate hollow cylindrical-type shaft 302 extending between a proximal end 304 and a distal end 306. A coupling portion 308 is provided adjacent distal end 306, and includes an internally threaded profile to engage connector portion 124 of handle mount 120. Other coupling arrangements between derotator handle 300 and handle mount 120 or transverse connecting member 102 are also contemplated, including non-threaded coupling arrangement, snap fits, interference fits, supplemental connectors such as a set screw, clamping arrangements, bayonet locks, and integral connections, for example. Coupling portion 308 can further include a distal socket 309 to allow handles 506, 508 to be employed as a tool during the surgical procedure. For example, socket 309 can be employed to tighten clamping assemblies 140 to connecting member 102 by positioning the socket portion 309 over a nut comprising a portion of securing portion 144.

Figures 17B, 17C:
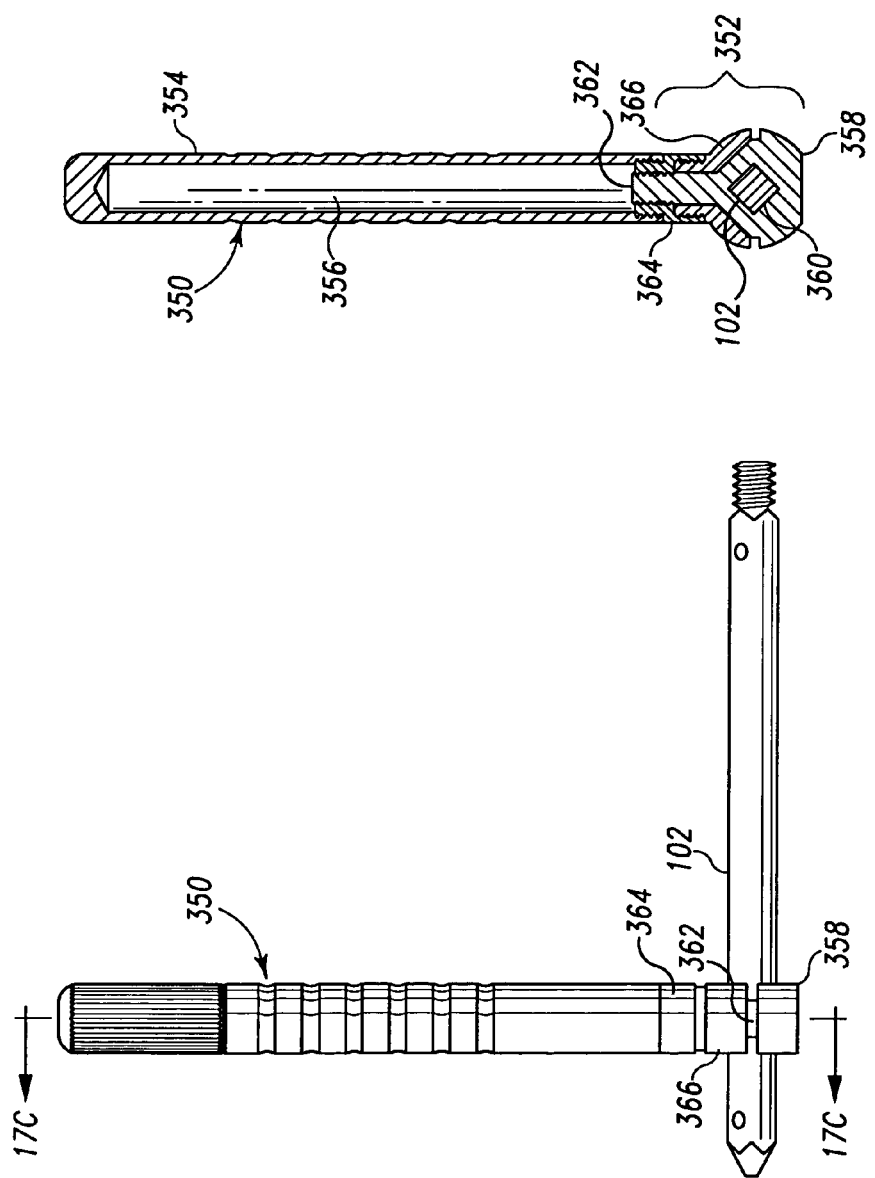
FIG. 17B is an elevation view of another embodiment derotation handle engaged to a transverse bridge.
FIG. 17C is a section view through line 17C-17C of FIG. 17B.

In FIGS. 17B-17C, another embodiment primary derotation handle 350 is shown coupled to connecting member 102 of transverse bridge 100. Handle 350 includes an elongate shaft 354 rotatably coupled to a distal clamping mount 352. Clamping mount 352 is positioned about and slidable along connecting member 102. Shaft 354 of handle 350 can be rotated for selectively loosening handle 350 for movement along connecting member 102 and then tightened by rotating shaft 354 to secure handle 350 in position along connecting member 102.

Clamping mount 352 includes a receiving member 358 for slidably receiving connecting element 102 through a passage 360 in a distal portion of receiving member 358. Receiving member 358 includes a proximal stem 362 coupled to shaft 354 with a coupling portion 364. Coupling portion 364 is secured to the distal end of shaft 354 and includes an internally threaded bore for threadingly engaging stem 362. A clamping member 366 extends about and is axially retained on coupling portion 364 such that shaft 354 and coupling portion 364 can be rotated without rotating clamping member 366. Furthermore, clamping member 366 extends outwardly from proximal stem 362 so clamping member 366 is adjacent to and in contactable with connecting member 102.

In use, clamping member 366 and receiving member 358 can be moved toward one another by threadingly advancing coupling portion 364 and shaft 354 along stem 362, forcing clamping member 366 against connecting member 102 and securing connecting member 102 in clamping engagement between clamping member 366 and receiving member 358. Handle 350 can be quickly released by rotating shaft 354 to unclamp connecting member 102 from between clamping member 366 and receiving member 358 when it is desired to reposition handle 350 along connecting member 102.

Figure 18A:
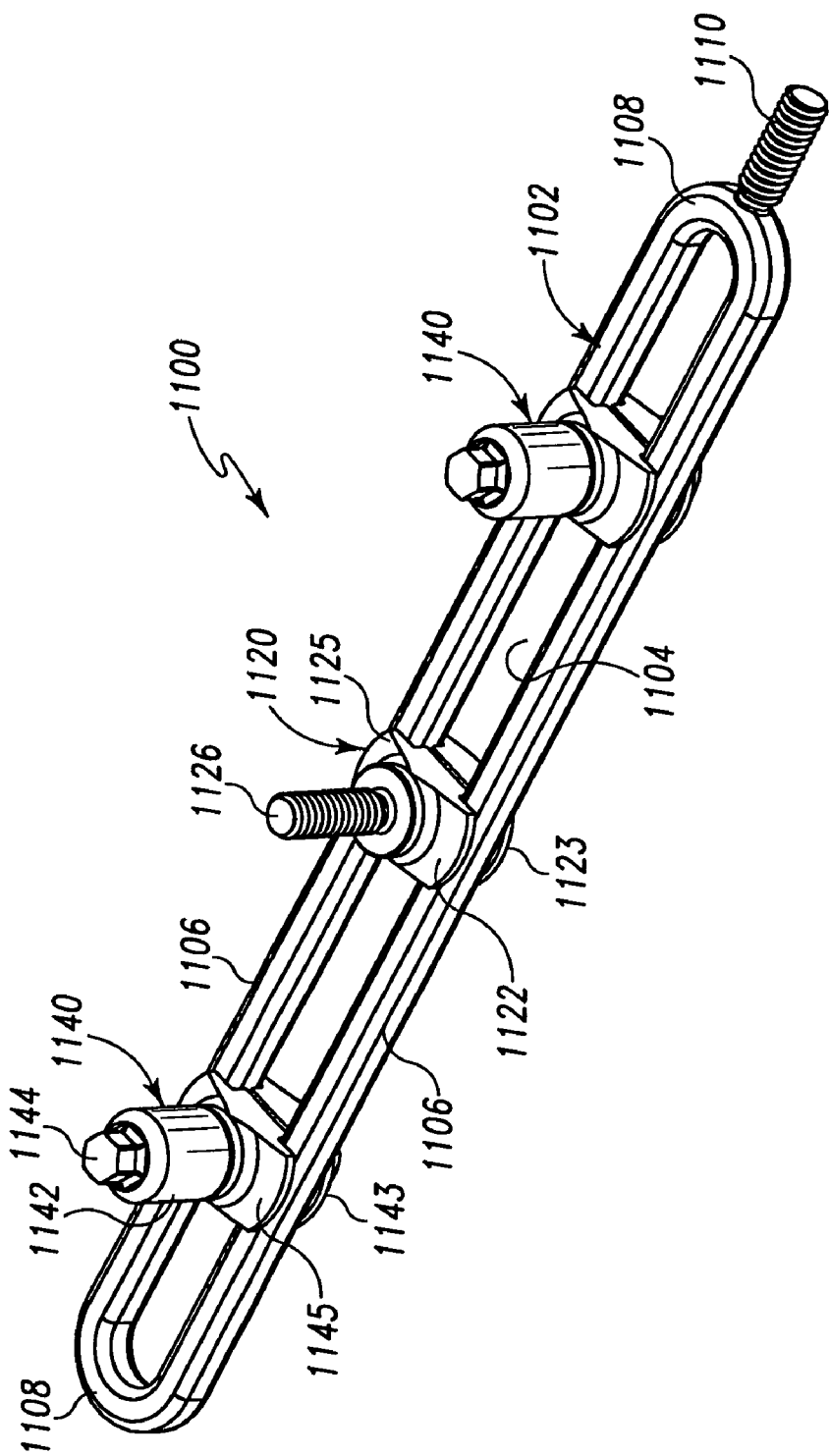
FIG. 18A is a perspective of another embodiment transverse bridge.
Figure 18B:
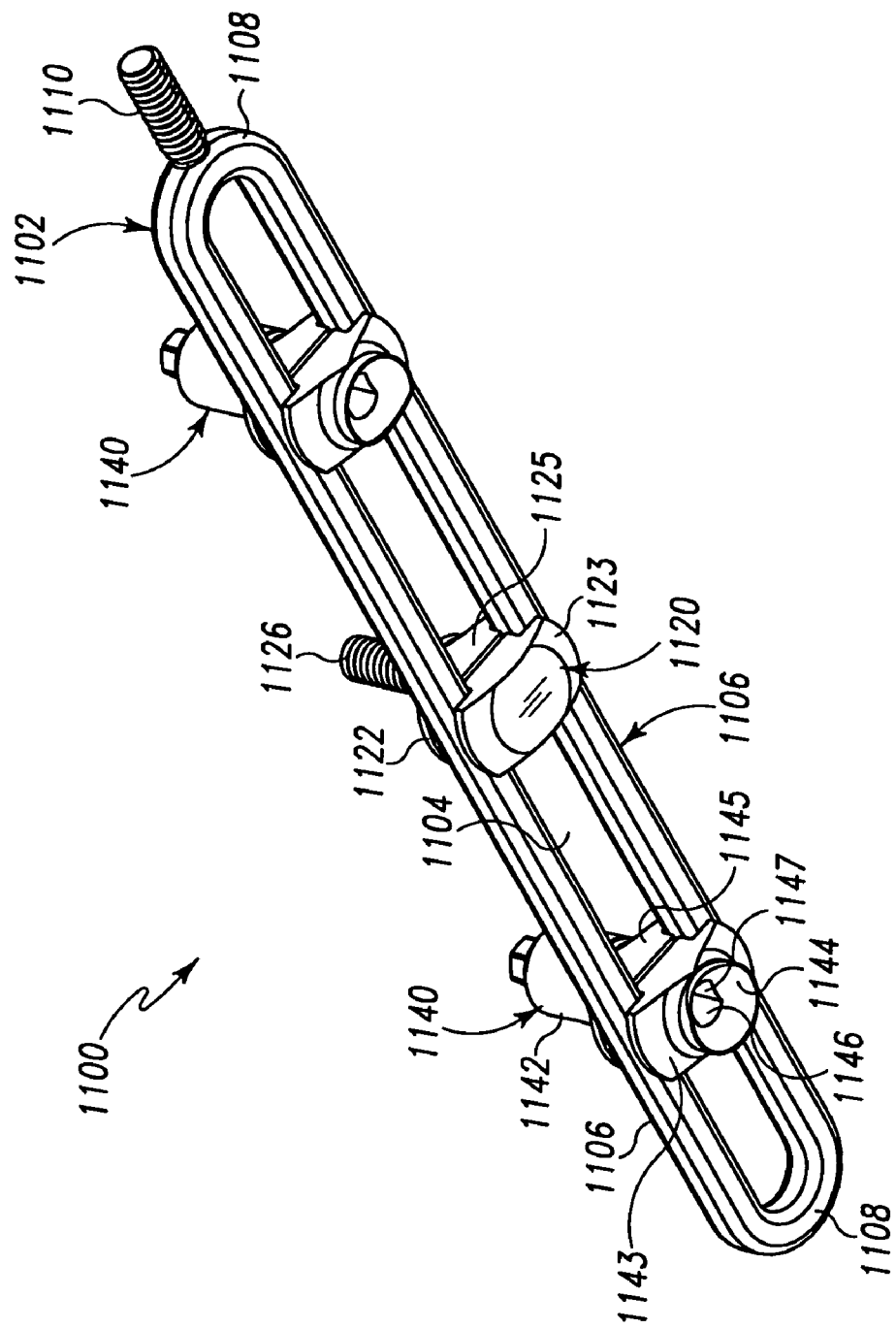
FIG. 18B is a perspective view looking toward the bottom of the transverse bridge of FIG. 18A.

Other embodiment transverse bridge, implant holders, derotation instrument assemblies and systems are also contemplated. For example, FIGS. 18A and 18B show a transverse bridge 1100 having a transverse connecting member in the form of a plate 1102. Plate 1102 is elongate and includes a central slot 1104 and side members 1106 extending therealong. The ends of the side members 1106 are connected by end members 1108. A connector portion 1110 extends from one of the end members 1108 for connection with a secondary derotation handle.

Transverse bridge 1100 includes a handle mount 1120 and clamp assemblies 1140 movable along and securable to plate 1102. Handle mount 1120 and clamp assemblies 1140 can be similar to those discussed above with respect to transverse bridge 100, but include oppositely extending clamping portions to clampingly engage each of the side members 1106 of plate 1102. For example, handle mount 1120 includes a body portion 1122 having an upper clamp half 1125 and a lower clamp half 1123 positionable on opposites sides of the side members 1106. A connector portion 1126 extends from lower clamp half 1123, and includes upper clamp half 1125 axially movable and axially retained thereabout. The derotation handle 300 can be secured to connector portion 1126 and into contact with upper clamp half 1125 to securely clamp plate 1102 between clamp halves 1123, 1125.

Similarly, clamping assemblies 1140 can include a clamping portion 1142 having an upper clamp half 1145 and a lower clamp half 1143. A securing portion 1144 extends through clamping portion 1142 and axially retains the clamping halves 1143, 1145 thereabout. Securing portion 1144 includes a bore 1146 with flats 1147 to non-rotatably receive post 82 therein. Securing portion 1144 is further rotatable within clamping portion 1142 to threadingly engage post 82 of implant holder 10. As securing portion 1144 is tightened onto implant holder 10, securing portion 1144 compresses clamping halves 1143, 1145 against the proximal end of implant holder 10 and thus toward one another for securement to side members 1106 of plate 1102.

Figure 19A:
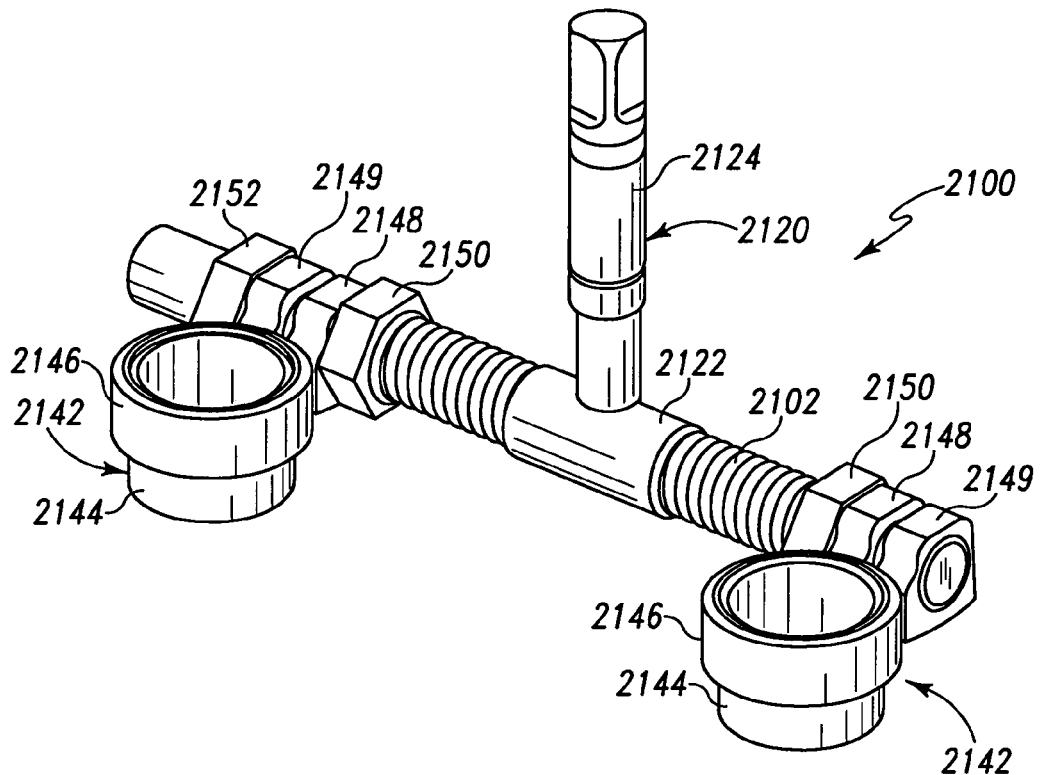
FIG. 19A is a perspective view of another embodiment transverse bridge.

A transverse bridge 2100 having a transverse connecting member in the form of a threaded transverse connecting rod 2102 having a length sized to extend between and be secured to implant holders is shown in FIG. 19A. A handle mount 2120 includes a body portion 2122 in the form of a sleeve positioned about and threadingly engaged to connecting member 2102. A connecting portion 2124 extends from body portion 2122 and is configured to receive a derotation handle thereover. In one embodiment, connecting portion 2124 can receive a quick connect type handle for ease of assembly. The positioning of handle mount 2120 along connecting member 2102 can be adjusted if desired by rotating body portion 2122 about connecting member 2102.

Transverse bridge 2100 further includes clamping assemblies 2140 at the ends of connecting member 2102 on opposite sides of handle mount 2120. Clamping assemblies 2140 each include a clamping portion 2142 that includes a sleeve 2144 positionable about implant holder 10, and a split-ring type clamping member 2146 that is moveable to release and securely engage sleeve 2144. Clamping member 2146 includes ends 2148, 2149 engaged to connecting member 2102. Ends 2148, 2149 are movable toward and away from one another by threading a respective clamping nut 2150 along connecting member 2102. The clamping nuts 2150 can compress ends 2148, 2149 together, which in turn tightly grips clamping member 2146 about sleeve 2144. Sleeve 2144 can be provided with a concave-convex interface with clamping member 2146 to provide angular adjustability between the implant holder and the clamping member 2146. In another embodiment, clamping member 2146 is clamped directly about a ball member, post, or other portion of the implant holder without sleeve 2144.

In the illustrated embodiment, one of the clamping members 2146 is fixed in position along connecting member 2102, while the other can be adjusted in position along connecting member 2102 by relocating an adjusting nut 2152 along connecting member 2102. Other embodiments contemplate that the positioning of both of clamping members 2146 can be adjustable along connecting member 2102.

Figure 19B:
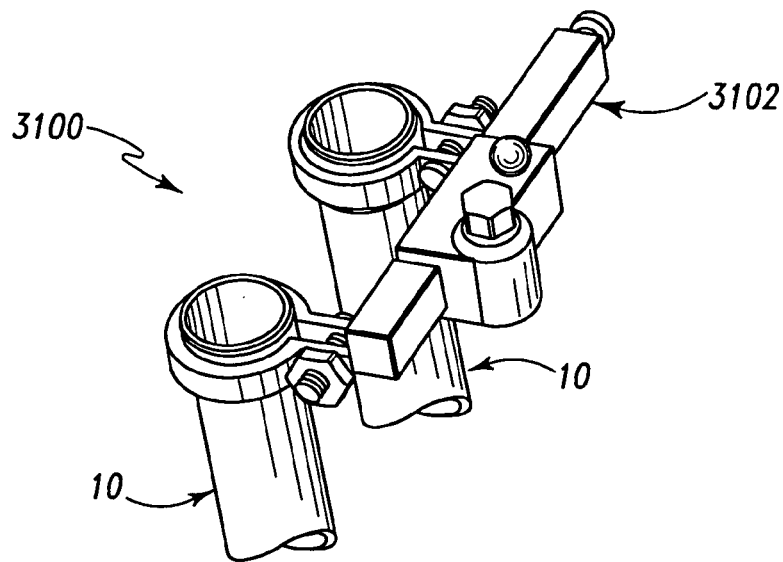
FIG. 19B is a perspective view of another embodiment transverse bridge and proximal portion of implant holders secured to one another with the transverse bridge.

FIG. 19B shows another embodiment transverse bridge 3100 having a connecting member in the form of a rack and pinion mechanism 3102 extending between implant holders 10. Rack and pinion mechanism 3102 can be engaged to the implant holders with clamping assemblies at the ends of the rack and pinion mechanism 3102. In one embodiment, rack and pinion mechanism can be the same or similar to that disclosed in U.S. Patent Application Publication No. 2003/0167059, which is incorporated herein by reference.

Figure 20:
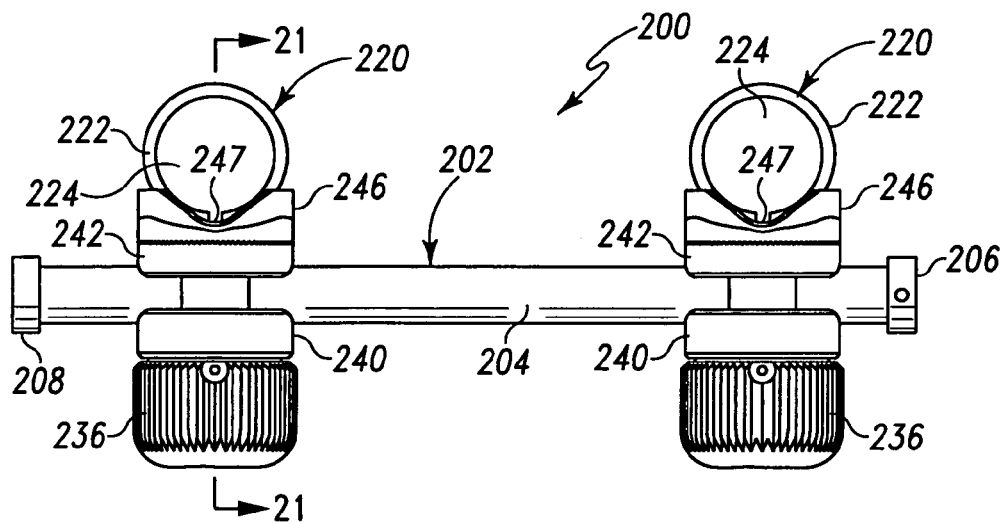
FIG. 20 is an elevation view of an inter-level linking assembly for linking derotation instrument assemblies.
Figure 21:
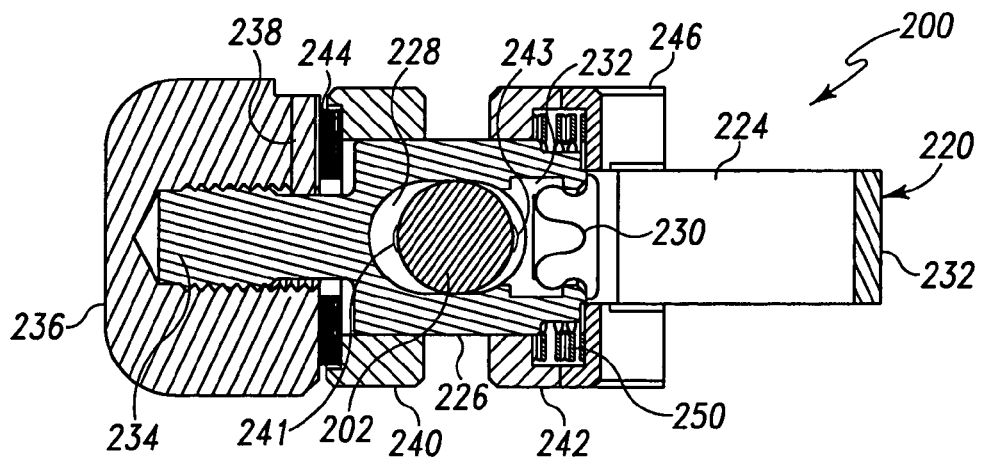
FIG. 21 is a section view through line 21-21 of FIG. 20 rotated 90 degrees from its FIG. 20 orientation.

Referring now to FIGS. 20-21, there is shown one embodiment of the inter-level linking assembly 510 in the form of inter-level linking assembly 200 having a link member 202 and connector assemblies 220. Inter-level linking assembly 200 is positionable to extend between and be coupled to portions of the system engaged to a vertebra or vertebrae of the vertebral level or vertebral levels to be aligned. For example, one or more connector assemblies 220 can be engaged to the respective primary handles, clamping assemblies, or the transverse handles. Linking of the one or more vertebral levels with inter-level linking assembly 200 allows corrective forces to distribute to multiple vertebral bodies and implants when applied with the primary or secondary derotation handles. Connector assemblies 220 can be moved along the length of link member 202 and secured at various positions therealong to accommodate the spacing between the components to be secured to inter-level linking assembly 200.

Link member 202 includes a rod or shaft-like body 204 extending between opposite ends 206, 208. Ends 206, 208 can include an enlarged, flange-like projection to prevent connector assemblies 220 from sliding off the ends thereof. Body 204 can include a circular cross-section as shown, or any other cross-sectional shape.

Connector assemblies 220 include a connector 222 having a passage 224 for receiving an element to which inter-level linking assembly 200 is to be connected, such as primary handle 300 as shown in FIG. 2. Connector 222 is coupled to a receiving member 226 with a clip 230 in a bore 232 at one end of receiving member 226. Clip 230 includes ears that extend into bore 232 and can deflect toward one another to facilitate assembly of connector 222. Furthermore, clip 230 is configured relative to bore 232 so that connector 222 can be rotated within bore 232. Receiving member 226 includes a central passage 228 through which link member 202 extends. The other end of receiving member 226 includes an extension 234 for threadingly receiving a clamping nut 236. A pin 238 in clamping nut 236 contacts the threads on extension 234 to prevent clamping nut 236 from being inadvertently removed.

Connector assembly 220 further includes a pair of clamping members 240, 242 that are moveable toward and away from one another to secure and release link member 202 therebetween. A washer 244 can be provided between clamping nut 236 and the first clamping member 240 to facilitate transfer of axial forces as clamping nut 236 is rotated.

A connector washer 246 is provided between second clamping member 242 and passage 224 of connector 222. A spring washer 250 or other suitable spring member between second clamping member 242 and connector washer 246 can bias clamping member 242 and connector washer 246 away from one another. Clamping nut 236 can be rotated along extension 234 to secure clamping members 240, 242 in clamping engagement on opposite sides of link member 202, securing connector assembly 220 in position along link member 202. In addition, the system element in passage 224 is pressed against connector washer 246, securing the element between connector 222 and connector washer 246.

A serrated, splined surface interface can be provided between second clamping member 242 and connector washer 246 to provide a locking arrangement therebetween when the element is engaged in passage 224. Spring 250 normally biases the serrated surfaces away from one another so that the surfaces do not contact one another and interfere with adjusting the orientation of connector 222 and connector washer 246 relative to clamping member 242 and link member 204. Clamping members 240, 242 can each include a recessed surface 241, 243, respectively, to receive link member 202 therein in nesting or substantially nesting engagement. In addition, connector washer 246 can include a recessed surface 247 to nestingly or substantially nestingly receive the portion of the element extending through passage 224 of connector 222.

Figure 22:
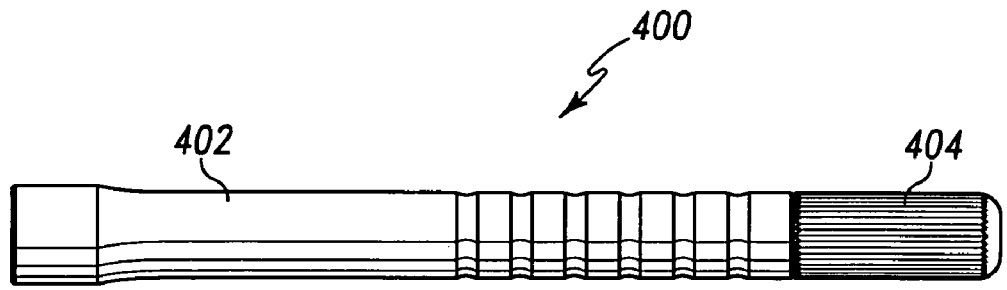
FIG. 22 is an elevation view of a handle extension engageable to an implant holder of FIG. 3.
Figure 23:
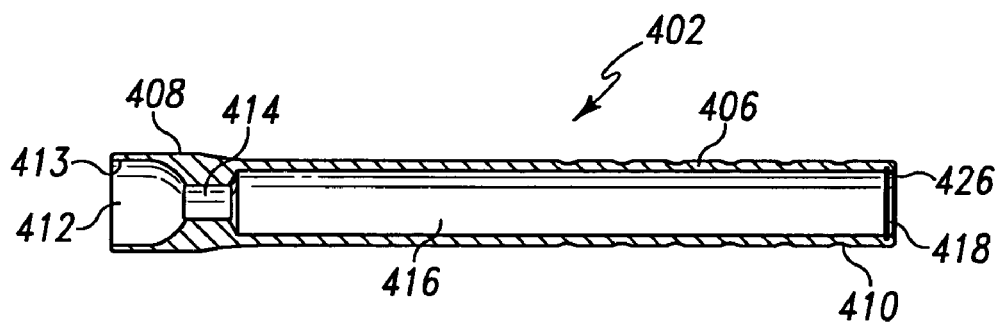
FIG. 23 is a longitudinal section view of an outer handle member of the handle extension of FIG. 22.
Figure 24:
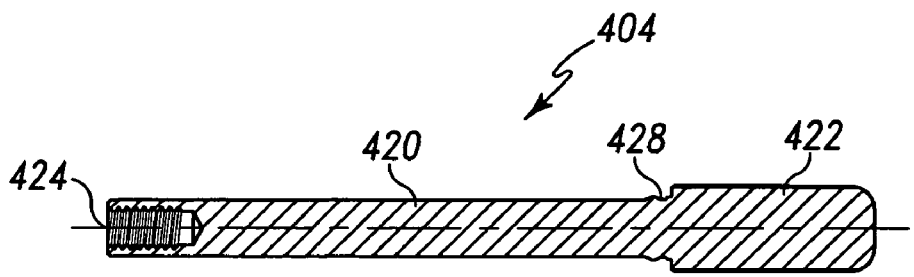
FIG. 24 is a longitudinal section view of an inner engaging member of the handle extension of FIG. 22.

It may further be desirable to provide a handle extension extending proximally from one or more of the implant holders 10 for selective manipulation of an implant holder 10 and the vertebra to which it is attached. In FIGS. 22-24 there is shown handle extension 400 comprising an outer handle member 402 and an inner engaging member 404. Outer handle member 402 includes an elongate, sleeve-like body 406 extending between a distal end 408 and a proximal end 410. Distal end 408 includes a distal opening 412 shaped like the proximal end cap of implant holder 10 for receipt thereof in form-fitting engagement. There is further provided a bore 414 through which the post 82 of implant holder 10 extends. Bore 414 extends between and opens in distal opening 412 and a central bore 416. Bore 414 can also be keyed like bore portion 143 discussed above to receive post 182 in form fitting and non-rotatable engagement.

Engaging member 404 includes a shaft like body 420 extending between a proximal handle end 422 and a distal bore 424. Body 420 can extend through outer handle member 402 with proximal handle end 422 extending proximally therefrom for access and grasping by the surgeon or attendant. Distal bore 424 is positioned proximally of bore 414 for engagement with the post 82 of implant holder 10. Bore 414 can be keyed to post 82 in form fitting engagement with flat surfaces 89 to prevent rotation of post 82 in bore 414. Engaging member 404 is axially retained but rotatable within outer handle member 402 with a retaining member 426 positioned between circumferential groove 418 formed in outer handle member 402 adjacent proximal end 410 thereof and circumferential groove 428 about engaging member 404 at the distal end of handle end 422.

In use, distal opening 412 is positioned about post 82 so that it extends through bore 414. Distal opening 412 has a distal cylindrical portion 413 that receives end cap 84 in a uni-axial manner so that handle extension 400 extends along the axis of implant holder 10 when engaged thereto. Handle extension 400 can be threadingly engaged to post 82 by rotating engaging member 404 and threading it along post 82. Handle extension 400 can be advanced along post 82 to seat end cap 84 in distal opening 412. Handle extension 400 is fixed to implant holder 10, and can be manipulated to apply corrective forces through implant holder 10 and the implant engaged to the vertebra.

In another embodiment, distal opening 412 does not include a cylindrical portion 413, but that has a spherical portion that opens directly at the distal end of handle extension 400. Post 82 can be adjusted to the desired angle relative to the remaining portion of implant holder 10. Handle extension 400 can then seated with its spherical end opening on the spherical end of end cap 84 in any one of a number of axial orientations relative to the axis of implant holder 10 and engaged in any one of such orientations by threaded engagement with post 82.

While the invention has been illustrated and described in detail in the drawings and foregoing description, the same is to be considered as illustrative and not restrictive in character. All changes and modifications that come within the spirit of the invention are desired to be protected.

What is claimed is:

1. A system for correcting alignment of one or more vertebrae of a spine, comprising:
    first and second implants engageable to one of the one or more vertebrae, said first and second implants being configured for engagement with respective ones of first and second stabilization elements positionable along the spine; and
    a derotation instrument assembly including first and second elongated implant holders releasably engaged to respective ones of said first and second implants, a transverse bridge positionable between and directly engaged to each of the first and second implant holders at a location spaced proximally from said first and second implants, and a primary derotation handle extending from said transverse bridge on a line directly between said first and second implant holders and orientable in a direction extending generally parallel to a sagittal plane of the spine, said primary derotation handle being associated with said bridge in a manner that permits forces applied to said handle to be directed to said transverse bridge, thereby manipulating said first and second implant holders at said location wherein said transverse bridge is engaged thereto and causing said first and second implant holders to manipulate said first and second implants when engaged to said first and second implant holders.

2. A system for correcting alignment of one or more vertebrae of a spine, comprising:
    first and second implants engageable to one of the one or more vertebrae, said first and second implants being configured for engagement with respective ones of first and second stabilization elements positionable along the spine; and
    a derotation instrument assembly including first and second elongated implant holders releasably engaged to respective ones of said first and second implants, a transverse bridge positionable between and directly engaged to each of the first and second implant holders at a location spaced proximally from said first and second implants, and a primary derotation handle extending from said transverse bridge at a location between said first and second implant holders and orientable in a direction extending generally parallel to a sagittal plane of the spine, said primary derotation handle being associated with said bridge in a manner that permits forces applied to said handle to be directed to said transverse bridge, thereby manipulating said first and second implant holders at said location wherein said transverse bridge is engaged thereto and causing said first and second implant holders to manipulate said first and second implants when engaged to said first and second implant holders, further comprising a secondary handle extending from an end of said transverse bridge in a direction substantially transversely oriented to said first and second implant holders and said primary derotation handle.

3. The system of claim 1, further comprising a second derotation instrument assembly including third and fourth elongated implant holders releasably engageable to respective ones of the third and fourth implants engageable to a second one of the one or more vertebrae, a second transverse bridge positionable between and engageable to each of the third and fourth implant holders at a location spaced proximally from said third and fourth implants, and a second primary derotation handle extending from said second transverse bridge at a location between said third and fourth implant holders and orientable in a direction extending generally parallel to the sagittal plane.

4. The system of claim 3, further comprising an inter-level linking assembly extending between and engaged to each of said primary derotation handles.

5. A system for correcting alignment of one or more vertebrae of a spine, comprising:
    first and second implants engageable to one of the one or more vertebrae, said first and second implants being configured for engagement with respective ones of first and second stabilization elements positionable along the spine;
    a derotation instrument assembly including first and second elongated implant holders releasably engaged to respective ones of said first and second implants, a transverse bridge positionable between and directly engaged to each of the first and second implant holders at a location spaced proximally from said first and second implants, and a primary derotation handle extending from said transverse bridge at a location between said first and second implant holders and orientable in a direction extending generally parallel to a sagittal plane of the spine, said primary derotation handle being associated with said bridge in a manner that permits forces applied to said handle to be directed to said transverse bridge, thereby manipulating said first and second implant holders at said location wherein said transverse bridge is engaged thereto and causing said first and second implant holders to manipulate said first and second implants when engaged to said first and second implant holders;
    a second derotation instrument assembly including third and fourth elongated implant holders releasable engageable to respective ones of the third and fourth implants engageable to a second one of the one or more vertebrae, a second transverse bridge positionable between and engageable to each of the third and fourth implant holders at a location spaced proximally from said third and fourth implants, and a second primary derotation handle extending from said second transverse bridge at a location between said third and fourth implant holders and orientable in a direction extending generally parallel to the sagittal plane; and
    an inter-level linking assembly extending between and engaged to each of said primary derotation handles, wherein said inter-level linking assembly includes an elongate link member extending between said primary derotation handles and connector assemblies movable along said link member and engageable to respective ones of said primary derotation handles to connect said primary derotation handles to said link member.

6. The system of claim 5, wherein said connector assemblies include:
   a connector defining a passage for receiving said respective primary derotation handles;
   a receiving member extending from said connector, said receiving member including a bore for receiving said link member therethrough in a transverse orientation to said primary derotation handles;
   a pair of clamping members about said receiving member on opposing first and second sides of said link member;
   a connector washer about said receiving member between said passage and said clamping member on said first side of said link member; and
   a clamping nut threadingly engageable along said receiving member on said second side of said link member with the other of said pair of clamping members between said clamping nut and said link member, said clamping nut being selectively operable to clamp said link member between said clamping members and said primary derotation handle between connector and said connector washer.

7. A system for correcting alignment of one or more vertebrae of a spine, comprising:
   first and second implants engageable to one of the one or more vertebrae, said first and second implants being configured for engagement with respective ones of first and second stabilization elements positionable along the spine; and
   a derotation instrument assembly including first and second elongated implant holders releasably engaged to respective ones of said first and second implants, a transverse bridge positionable between and directly engaged to each of the first and second implant holders at a location spaced proximally from said first and second implants, and a primary derotation handle extending from said transverse bridge at a location between said first and second implant holders and orientable in a direction extending generally parallel to a sagittal plane of the spine, said primary derotation handle being associated with said bridge in a manner that permits forces applied to said handle to be directed to said transverse bridge, thereby manipulating said first and second implant holders at said location wherein said transverse bridge is engaged thereto and causing said first and second implant holders to manipulate said first and second implants when engaged to said first and second implant holders, wherein said transverse bridge includes:
   an elongated connecting member positionable between said implant holders;
   first and second clamping assemblies extending between said connecting member and respective ones of said first and second implant holders to couple said connecting member to said respective implant holder; and
   a handle mount engaged to said connecting member between said first and second clamping assemblies, said primary derotation handle extending from said handle mount.

8. The system of claim 7, wherein said primary handle is removably coupled to said handle mount.

9. The system of claim 7, wherein said handle mount is movable along said connecting member between said clamp assemblies.

10. The system of claim 7, wherein said first and second clamping assemblies each include:
    a clamping portion including a bore for receiving a proximal post extending from said respective implant holder, said clamping portion further including a pair of arms extending therefrom for receiving said connecting member therebetween; and
    a securing portion rotatably mounted to a proximal end of said clamping portion and removably engageable to said post of said respective implant holder, wherein said securing portion is operable to move said pair of arms toward one another to engage said connecting member between said pair of arms as said securing member is engaged to said proximal post thereby clamping said clamping portion between said securing member and said respective implant holder.

11. The system of claim 10, wherein clamping portion includes a hinge portion opposite said pair of arms and said pair of arms are movable about said hinge portion.

12. The system of claim 7, wherein said connecting member includes an elongated plate positionable between said implant holders and having at least one opening therethrough.

13. The system of claim 12, wherein said at least one opening includes an elongated slot with side members extending along said slot and end members extending between said side members and said handle mount and said clamping assemblies are mounted in said slot.

14. The system of claim 7, wherein said connecting member includes an elongated threaded rod positionable between said implant holders.

15. The system of claim 7, wherein said connecting member includes a rack and pinion mechanism positionable between said implant holders.

16. The system of claim 7, wherein said connecting member includes a non-circular cross-section along a substantial portion of a length thereof.

17. A system for correcting alignment of one or more vertebrae of a spine, comprising:
    first and second implants engageable to one of the one or more vertebrae, said first and second implants being configured for engagement with respective ones of first and second stabilization elements positionable along the spine;
    a derotation instrument assembly including first and second elongated implant holders releasably engageable to respective ones of said first and second implants, wherein at least one of said implant holders includes a first arm and a second arm extending along a longitudinal axis, said first and second arms each being pivotally connected to one another with distal portions thereof offset to a first side of said longitudinal axis and movable between a closed position in clamping engagement with a respective one of said first and second implants and an open position for releasing said respective implant, said derotation instrument assembly further including a transverse bridge positionable between and engageable to each of said first and second implant holders at a location spaced proximally from said first and second implants and proximally of said pivotal connection of said arms of said at least one implant holder; and
    a derotation handle engaged to said transverse bridge.

18. The system of claim 17, wherein said derotation handle extends from said transverse bridge at a location between said first and second implant holders and in a direction extending generally parallel to a sagittal plane of the spine and said first and second implant holders.

19. The system of claim 17, wherein said distal end portions further define an opening along one side thereof oriented away from said longitudinal axis.

20. The system of claim 19, wherein said distal end portions are movable toward one another to grip said implant therebetween by pivoting a proximal end of said second arm toward said first arm.

21. The system of claim 20, wherein said distal end portions each include a projection extending toward the other of said distal end portions, said projection being received in detents in said implant when said implant holder is in a closed position.

22. The system of claim 17, wherein said at least one implant holder includes a latching mechanism for locking said first and second arms in said closed position.

23. The system of claim 17, wherein said first and second arms are spring biased toward said open position.

24. The system of claim 17, wherein said first arm includes a length along said longitudinal axis that is greater than a length of said second arm along said longitudinal axis, wherein said first arm includes a post extending proximally from a proximal end thereof for engagement with a portion of said transverse bridge.

25. The system of claim 24, wherein said first arm includes an end cap at said proximal end thereof, said end cap defining a receptacle and said post including a ball end pivotally captured in said receptacle, said post further including a post portion extending proximally through said end cap in pivotal relation to said first arm of said implant holder.

26. The system of claim 25, wherein said portion of said transverse bridge includes a clamping assembly, said clamping assembly including:
a clamping portion including a bore for receiving said proximal post extending from said at least one implant holder, said clamping portion further including a pair of arms extending therefrom for receiving a connecting member of said transverse bridge therebetween; and
a securing portion rotatably mounted to a proximal end of said clamping portion and removably engageable to said post of said at least one implant holder, wherein said securing portion is operable to move said pair of arms toward one another to engage said connecting member between said pair of arms as said securing member is engaged to said proximal post thereby clamping said clamping portion between said securing member and said end cap of said at least one implant holder.

27. The system of claim 26, wherein clamping portion includes a hinge portion opposite said pair of arms and said pair of arms are movable about said hinge portion.

28. A system for correcting alignment of one or more vertebrae of a spine, comprising:
first and second implants engageable to respective first and second vertebrae, said first and second implants being configured for engagement with a stabilization element positionable along the spine;
a first derotation instrument assembly including a first implant holder releasably engageable to said first implant, a first transverse bridge directly engaged to a proximal end of said first implant holder, said first transverse bridge extending from said first implant holder to another implant holder for engagement with the another implant holder;
a second derotation instrument assembly including a second implant holder releasably engageable to said second implant, a second transverse bridge directly engaged to a proximal end of said second implant holder, said second transverse bridge extending from said second implant holder to another implant holder for engagement with the another implant holder; and
an inter-level linking assembly coupled to said first and second transverse bridges at a location between said implant holders of each of said first and second derotation instrument assemblies.

29. The system of claim 28, wherein each of said implant holders includes a pivotal post extending proximally therefrom and said first and second transverse bridges are coupled with said pivotal post of said respective first and second implant holders.

30. The system of claim 28, further comprising:
a first primary derotation handle extending from said first transverse bridge at a location spaced from said first implant holder, said first primary handle extending generally parallel to a sagittal plane of the spine;
a second primary derotation handle extending from said second transverse bridge at a location spaced from said second implant holder, said second primary handle extending generally parallel to the sagittal plane; and
said inter-level linking assembly includes first and second connecting assemblies coupled to respective ones of said first and second primary derotation handles, said inter-level linking assembly further including a link member extending between and engaged to said connecting assemblies.

31. The system of claim 30, wherein at least one of said first and second connecting assemblies is movable along said link member and securable to said link member at any one of a number of positions therealong to adjust a spacing between said connecting assemblies.

32. The system of claim 30, wherein said connector assemblies include:
a connector defining a passage for receiving said respective primary derotation handles;
a receiving member extending from said connector, said receiving member including a bore for receiving said link member therethrough in a transverse orientation to said primary derotation handles;
a pair of clamping members about said receiving member on opposing first and second sides of said link member;
a connector washer about said receiving member between said passage and said clamping member on said first side of said link member; and
a clamping nut threadingly engageable along said receiving member on said second side of said link member with the other of said pair of clamping members between said clamping nut and said link member, said clamping nut being selectively operable to clamp said link member between said clamping members and said primary derotation handle between connector and said connector washer.

* * * * *